(12) United States Patent
Prochiantz et al.

(10) Patent No.: US 10,722,554 B2
(45) Date of Patent: Jul. 28, 2020

(54) METHODS OF REDUCING EXCITOTOXICITY-INDUCED RETINAL GANGLIONIC NEURON DEGENERATION BY AN ORTHODENTICLE HOMOLOG2 (OTX2) HOMEOPROTEIN

(75) Inventors: Alain Prochiantz, Paris (FR); Kenneth Lee Moya, Clichy (FR)

(73) Assignees: Centre National de la Recherche Scientifique, Paris (FR); Ecole Normale Superieure, Paris (FR)

(*) Notice: Subject to any disclaimer, the term of this patent is extended or adjusted under 35 U.S.C. 154(b) by 980 days.

(21) Appl. No.: 12/812,139

(22) PCT Filed: Jan. 9, 2009

(86) PCT No.: PCT/FR2009/000031
§ 371 (c)(1),
(2), (4) Date: Nov. 17, 2010

(87) PCT Pub. No.: WO2009/106767
PCT Pub. Date: Sep. 3, 2009

(65) Prior Publication Data
US 2011/0065646 A1    Mar. 17, 2011

(30) Foreign Application Priority Data
Jan. 9, 2008 (FR) ................................... 08 00110

(51) Int. Cl.
| | | |
|---|---|---|
| A61K 38/00 | (2006.01) | |
| A61K 38/18 | (2006.01) | |
| A61K 38/19 | (2006.01) | |
| A61K 38/20 | (2006.01) | |
| A61K 38/21 | (2006.01) | |
| A61K 38/17 | (2006.01) | |
| C07K 14/47 | (2006.01) | |
| C07K 14/475 | (2006.01) | |
| C07K 14/48 | (2006.01) | |
| C07K 14/00 | (2006.01) | |
| C07K 7/00 | (2006.01) | |
| C07K 5/00 | (2006.01) | |
| A61P 25/28 | (2006.01) | |
| C12N 5/079 | (2010.01) | |
| A61K 35/30 | (2015.01) | |
| A61K 9/00 | (2006.01) | |
| C12N 15/85 | (2006.01) | |
| G01N 33/50 | (2006.01) | |
| A61L 27/38 | (2006.01) | |
| C12N 15/63 | (2006.01) | |
| C12N 5/0793 | (2010.01) | |
| C12N 15/90 | (2006.01) | |
| A61P 27/02 | (2006.01) | |
| A61L 27/54 | (2006.01) | |
| G01N 33/569 | (2006.01) | |
| A61F 2/14 | (2006.01) | |
| G01N 33/68 | (2006.01) | |

(52) U.S. Cl.
CPC ............... *A61K 38/17* (2013.01); *A61F 2/14* (2013.01); *A61K 9/0048* (2013.01); *A61K 9/0051* (2013.01); *A61K 35/30* (2013.01); *A61K 38/00* (2013.01); *A61K 38/1709* (2013.01); *A61K 2300/00* (2013.01); *A61L 27/383* (2013.01); *A61L 27/54* (2013.01); *A61L 2300/64* (2013.01); *A61P 25/28* (2018.01); *A61P 27/02* (2018.01); *C07K 14/00* (2013.01); *C07K 14/47* (2013.01); *C07K 14/4702* (2013.01); *C07K 2319/33* (2013.01); *C12N 5/062* (2013.01); *C12N 5/0618* (2013.01); *C12N 5/0619* (2013.01); *C12N 5/0621* (2013.01); *C12N 15/63* (2013.01); *C12N 15/85* (2013.01); *C12N 15/907* (2013.01); *C12N 2500/32* (2013.01); *C12N 2501/40* (2013.01); *C12N 2501/60* (2013.01); *C12N 2502/085* (2013.01); *C12N 2533/50* (2013.01); *C12N 2830/85* (2013.01); *G01N 33/5014* (2013.01); *G01N 33/5058* (2013.01); *G01N 33/56966* (2013.01); *G01N 33/6896* (2013.01); *G01N 2333/46* (2013.01); *G01N 2800/168* (2013.01); *Y02A 90/26* (2018.01)

(58) Field of Classification Search
CPC .. A61K 38/17; A61K 47/48238; A61K 38/00; A61K 35/30; C07K 14/47; C12N 5/0619; C12N 5/0621; C12N 2830/85; G01N 33/5058; G01N 33/6896
See application file for complete search history.

(56) References Cited

U.S. PATENT DOCUMENTS

| | | | | |
|---|---|---|---|---|
| 7,541,186 B2 * | 6/2009 | Reh et al. | ...................... | 435/377 |
| 7,858,346 B2 * | 12/2010 | Furukawa | .................... | 435/70.3 |
| 2006/0122111 A1 * | 6/2006 | Furukawa | ........................ | 514/12 |

(Continued)

FOREIGN PATENT DOCUMENTS

EP    1 591 127    11/2005

OTHER PUBLICATIONS

Burgess et al. J of Cell Bio. 1990, 111:2129-2138.*

(Continued)

*Primary Examiner* — Chang-yu Wang
(74) *Attorney, Agent, or Firm* — Morgan, Lewis Bockius LLP

(57) ABSTRACT

The invention relates to the use of a homeoprotein of the bicoid family, in particular of the Otx family, for enhancing the survival of cultivated retinal ganglion neurones, and for preventing or treating ganglion neuron degeneration particularly occurring in glaucoma.

8 Claims, 3 Drawing Sheets
Specification includes a Sequence Listing.

(56) References Cited

U.S. PATENT DOCUMENTS

2008/0233648 A1* 9/2008 Sugaya et al. ............... 435/377
2012/0015884 A1* 1/2012 Prochiantz et al. ......... 514/17.7
2017/0080060 A1* 3/2017 Prochiantz ......... C07K 14/4702

OTHER PUBLICATIONS

Bowie et al. Science, 1990, 247:1306-1310.*
Pawson et al. 2003, Science 300:445-452.*
Berson, Pflugers Arch-Eur J. Physiolol. 2007, 454:849-855.*
Ullian et al. Mol. Cell. Neurosci. 2004; 26:544-557.*
Kendell et al. Invest Ophthalmol Vis Sci. 1995; 36:200-205.*
Quigley, Arch Ophthalmol.2001; 119; 1390.*
The factsheet of P32243 Otx2 from the UniPort website: https://www.uniprot.org/uniprot/P32243.*
Sigurdsson et al., Acta Ophthalmol. Scand. 2007; 85:598-602.*
Kim et al., Invest. Ophthalmol. Vis. Sci. 2004; 45:2722-2731.*
Santvliet et al. Surv. Ophthalmol. 2004; 49:197-212.*
Nishida, et al., "Otx2 Homeobox Gene Controls Retinal Photoreceptor Cell Fate and Pineal Gland Development", Nature Neuroscience, 6, pp. 1255-1263, 2003.
Sakami, et al., "Expression of Otx2 During Regeneration and Development of Newt Retina", Zoological Science, 18, p. 64, 2001.
Rath, et al., "Ontogenetic Expression of Otx2 and Crx Homeobox Genes in the Retina of the Rat", Experimental Eye Research, 85, pp. 65-73, 2007.

* cited by examiner

SEQUENCE LISTING

```
<160> NUMBER OF SEQ ID NOS: 2

<210> SEQ ID NO 1
<211> LENGTH: 289
<212> TYPE: PRT
<213> ORGANISM: Homo sapiens
<220> FEATURE:
<221> NAME/KEY: DOMAIN
<222> LOCATION: (38)..(97)
<223> OTHER INFORMATION: Homeodomain

<400> SEQUENCE: 1

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
            20                  25                  30

Ala Thr Pro Arg Lys Gln Arg Arg Glu Arg Thr Thr Phe Thr Arg Ala
        35                  40                  45

Gln Leu Asp Val Leu Glu Ala Leu Phe Ala Lys Thr Arg Tyr Pro Asp
    50                  55                  60

Ile Phe Met Arg Glu Glu Val Ala Leu Lys Ile Asn Leu Pro Glu Ser
65                  70                  75                  80

Arg Val Gln Val Trp Phe Lys Asn Arg Arg Ala Lys Cys Arg Gln Gln
                85                  90                  95

Gln Gln Gln Gln Gln Asn Gly Gly Gln Asn Lys Val Arg Pro Ala Lys
            100                 105                 110

Lys Lys Thr Ser Pro Ala Arg Glu Val Ser Ser Glu Ser Gly Thr Ser
        115                 120                 125

Gly Gln Phe Thr Pro Pro Ser Ser Thr Ser Val Pro Thr Ile Ala Ser
    130                 135                 140

Ser Ser Ala Pro Val Ser Ile Trp Ser Pro Ala Ser Ile Ser Pro Leu
145                 150                 155                 160

Ser Asp Pro Leu Ser Thr Ser Ser Ser Cys Met Gln Arg Ser Tyr Pro
                165                 170                 175

Met Thr Tyr Thr Gln Ala Ser Gly Tyr Ser Gln Gly Tyr Ala Gly Ser
            180                 185                 190

Thr Ser Tyr Phe Gly Gly Met Asp Cys Gly Ser Tyr Leu Thr Pro Met
        195                 200                 205

His His Gln Leu Pro Gly Pro Gly Ala Thr Leu Ser Pro Met Gly Thr
    210                 215                 220

Asn Ala Val Thr Ser His Leu Asn Gln Ser Pro Ala Ser Leu Ser Thr
225                 230                 235                 240

Gln Gly Tyr Gly Ala Ser Ser Leu Gly Phe Asn Ser Thr Thr Asp Cys
                245                 250                 255
```

```
Leu Asp Tyr Lys Asp Gln Thr Ala Ser Trp Lys Leu Asn Phe Asn Ala
            260                 265                 270

Asp Cys Leu Asp Tyr Lys Asp Gln Thr Ser Ser Trp Lys Phe Gln Val
            275                 280                 285

Leu

<210> SEQ ID NO 2
<211> LENGTH: 297
<212> TYPE: PRT
<213> ORGANISM: Homo sapiens
<220> FEATURE:
<221> NAME/KEY: DOMAIN
<222> LOCATION: (32)..(97)
<223> OTHER INFORMATION: Homeodomain
<220> FEATURE:
<221> NAME/KEY: DOMAIN
<222> LOCATION: (46)..(105)
<223> OTHER INFORMATION: Homeodomain

<400> SEQUENCE: 2

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
            20                  25                  30

Gly Pro Trp Ala Ser Cys Pro Ala Ala Thr Pro Arg Lys Gln Arg Arg
            35                  40                  45

Glu Arg Thr Thr Phe Thr Arg Ala Gln Leu Asp Val Leu Glu Ala Leu
    50                  55                  60

Phe Ala Lys Thr Arg Tyr Pro Asp Ile Phe Met Arg Glu Glu Val Ala
65                  70                  75                  80

Leu Lys Ile Asn Leu Pro Glu Ser Arg Val Gln Val Trp Phe Lys Asn
                85                  90                  95

Arg Arg Ala Lys Cys Arg Gln Gln Gln Gln Gln Gln Asn Gly Gly
                100                 105                 110

Gln Asn Lys Val Arg Pro Ala Lys Lys Lys Thr Ser Pro Ala Arg Glu
            115                 120                 125

Val Ser Ser Glu Ser Gly Thr Ser Gly Gln Phe Thr Pro Pro Ser Ser
    130                 135                 140

Thr Ser Val Pro Thr Ile Ala Ser Ser Ser Ala Pro Val Ser Ile Trp
145                 150                 155                 160

Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
            180                 185                 190

Tyr Ser Gln Gly Tyr Ala Gly Ser Thr Ser Tyr Phe Gly Gly Met Asp
    195                 200                 205

Cys Gly Ser Tyr Leu Thr Pro Met His His Gln Leu Pro Gly Pro Gly
210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Phe Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
    275                 280                 285
```

```
Thr Ser Ser Trp Lys Phe Gln Val Leu
    290                 295
```

METHODS OF REDUCING EXCITOTOXICITY-INDUCED RETINAL GANGLIONIC NEURON DEGENERATION BY AN ORTHODENTICLE HOMOLOG2 (OTX2) HOMEOPROTEIN

RELATED APPLICATIONS

The present application is a U.S. National Phase Application of International Application No. PCT/FR2009/000031 (filed Jan. 9, 2009) which claims priority to French Patent Application No. 0800110 (filed Jan. 9, 2008) which are hereby incorporated by reference in their entirety.

SEQUENCE LISTING SUBMISSION VIA EFS-WEB

A computer readable text file, entitled "045636-5143-SequenceListing.txt," created on or about Jul. 8, 2010 with a file size of about 6 kb contains the sequence listing for this application and is hereby incorporated by reference in its entirety.

BACKGROUND

The present invention relates to the treatment of diseases involving a retinal ganglion neuron (RGC) degeneration, and in particular glaucoma.

The retina is the cell sheet which covers the back of the eye. It contains various types of neurons, the role of which is to capture light energy and to convert it into a nerve signal, and also glial cells.

Schematically, the retina comprises three main layers of neurons: photoreceptor neurons (cones and rods), bipolar neurons and ganglionic neurons; other neurons, amacrine neurons and horizontal neurons, play a regulatory role. The photoreceptor neurons react to light, and the signal that they generate is transmitted, by means of the bipolar neurons, to the ganglionic neurons, the axons of which constitute the nerve fibers of the optic nerve, ensuring that the information is sent to the brain.

Retinal neuron degeneration is involved in various retinopathies. Thus, photoreceptor neuron degeneration is involved in certain pathological conditions, such as retinitis pigmentosa or macular degeneration. In other pathological conditions, it is the ganglionic neurons which are affected. Damage to retinal ganglion neurons can be observed in various genetic or vascular optical neuropathies, but also more broadly in the context of neurodegenerative diseases (such as, for example, Alzheimer's disease, multiple sclerosis or Parkinson's disease).

One of the pathological conditions in which the predominant role of damage to the retinal ganglion neurons has been demonstrated is glaucoma. In this pathological condition, the degeneration of these neurons and of their axons results in a slow deterioration of the optic nerve, which can result in total blindness. The most common cause of glaucoma is intraocular hypertension. Although the mechanisms resulting in the destruction of ganglionic neurons are still poorly elucidated, its involvement in the occurrence of the pathological condition has been shown (Nickells, 2007, Can. J. Ophthalmol., 42, 278-87). In addition, in patients suffering from glaucoma, excessive concentrations of glutamate, a neurotransmitter normally present in the vitreous humor, have been observed (Dreyer et al., Arch Ophthalmol, 114, 299-305, 1996) (Morrison et al., Prog Retin Eye Res, 24, 217-240, 2005). At these concentrations, glutamate has a neurotoxic activity on ganglionic neurons in culture or in vivo (Hahn et al., Proc Natl Acad Sci USA, 85, 6556-6560, 1988; Li et al., Invest Ophthalmol V is Sci, 40, 1004-1008, 1999) (Shen and Slaughter, J Neurophysiol, 87, 1629-1634, 2002). TNF-alpha is also overexpressed in the retina and the optic nerve of patients suffering from glaucoma (Yuan and Neufeld, Glia, 32, 42-50, 2000; Tezel et al., Invest Ophthalmol V is Sci, 42, 1787-1794, 2001). The toxicity of this cytokine, associated with the presence of receptors on the ganglionic neurons, has been demonstrated in vitro (Fuchs et al., Invest Ophthalmol V is Sci, 46, 2983-2991, 2005) and in vivo (Fontaine et al., J Neurosci, 22, RC216, 2002).

The treatments currently available for glaucoma are based on molecules capable of reducing intraocular pressure (Woodward and Chen, Expert Opin Emerg Drugs, 12, 313-327, 2007).

Homeoproteins, or homeodomain proteins, are transcription factors which play a major role in the cell migration and differentiation phenomena involved in morphogenesis of the organism. They are characterized by the presence of a sequence of 60 amino acids, the homeoprotein, which is a DNA-binding domain, having a particular structure (helix/turn/helix). It has been shown that the isolated homeodomain of the Antennapedia protein of *Drosophila* can, firstly, cross the membrane of neurons in culture and, secondly, accumulate in the nucleus and promote neurite growth (application EP0485578 (Joliot et al., Proc Natl Acad Sci USA, 88, 1864-1868, 1991)). The penetration properties of the Antennapedia homeodomain are conferred by its third helix, and appear to be highly conserved between homeoproteins; its properties on neurite growth appear to be correlated with its DNA-binding properties, at the level of binding sites defined by the consensus sequence ANNNNCATTA (application EP0485578 (Joliot et al., Proc Natl Acad Sci USA, 88, 1864-1868, 1991)).

Otx2 (orthodenticle homolog 2) is a homeoprotein containing a bicoid-type homeodomain (Simeone et al., Embo J, 12, 2735-2747, 1993). It belongs to the Otx homeoprotein family, which plays a fundamental role in brain development during embryogenesis (Acampora et al., Prog Neurobiol, 64, 69-95, 2001; Simeone et al., Curr Opin Genet Dev, 12, 409-415, 2002). It has also been shown that Otx2 is involved in the formation of the retina, by promoting the differentiation of retinal stem cells into photoreceptor neurons. Application EP1591127 thus reports that transformation of retinal stem cells with a recombinant vector expressing Otx2 induces the differentiation of these cells into photoreceptor neurons, to the detriment of the other types of retinal neurons, and proposes the use of Otx2 for treating various retinal pathological conditions involving photoreceptor neuron degeneration.

DETAILED DESCRIPTION

Figure 1:
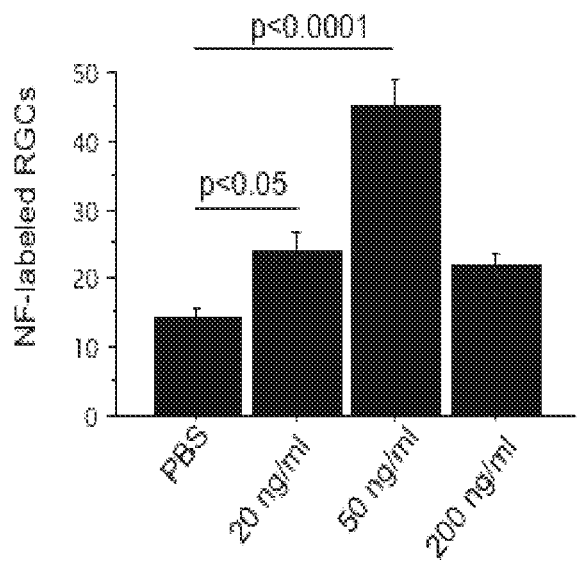
FIG. 1 is the results obtained from mixed cultures of dissociated adult retinal cells.

The inventors have now demonstrated a novel effect of Otx2, which does not manifest itself at the level of retinal neuron differentiation, but at the level of the survival of already differentiated adult neurons, and which concerns ganglionic neurons. They have in fact observed that the addition of Otx2 to cultures of axotomized adult ganglionic neurons (which normally die very rapidly) enables their survival.

This new property of Otx2 makes it possible to propose its use, and more generally that of the homeoproteins of the bicoid family, and in particular of the Otx subfamily, for improving the survival of adult ganglionic neurons in culture in vitro, and also for preventing or treating, in vivo, ganglionic neuron degeneration.

The term: "homeoprotein of the bicoid family" is herein intended to mean any homeoprotein of which the homeodomain has at least 35% sequence identity with that of human Otx2 protein (residues 38-97 of the sequence SEQ ID NO: 1), and which contains a lysine residue at position of said homeodomain. Among these proteins of the bicoid family, the term "homeoprotein of the Otx subfamily" defines any homeoprotein of which the homeodomain has at least 80% identity, preferably at least 85% identity, and entirely preferably at least 90% identity with that of the human Otx2 protein, and, among this Otx subfamily, the term "Otx2 homeoprotein" defines any homeoprotein of which the homeodomain has at least 98% sequence identity with that of the human Otx2 protein, and the overall polypeptide sequence of which has at least 90%, preferably at least 95% identity with the protein SEQ ID NO: 1 (corresponding to isoform 1 of the human Otx2 protein, with reference on SwissProt under number P32243), or with the protein SEQ ID NO: 2 (corresponding to isoform 2 of the human Otx2 protein, referenced on SwissProt under number P32243-2).

Said homeoprotein can be readily obtained by methods well known in themselves. It can, for example, be produced in recombinant form by means of conventional genetic engineering methods.

The subject of the present invention is thus a method for improving the survival of ganglionic neurons, characterized in that it comprises bringing a homeoprotein of the Otx subfamily, and in particular an Otx2 homeoprotein, or a composition comprising said homeoprotein, into contact with said ganglionic neurons.

More specifically, the subject of the present invention is the use of a homeoprotein of the bicoid family, preferably of a homeoprotein of the Otx subfamily, and in particular of an Otx2 homeoprotein, or of a composition comprising said homeoprotein, for obtaining a medicament for the prevention or treatment of ganglionic neuron degeneration, and more particularly of such a degeneration occurring in glaucoma.

Thus, the subject of the present invention is a method for treating a patient exhibiting ganglionic neuron degeneration, for example a patient suffering from glaucoma, characterized in that it comprises the administration to said patient of a homeoprotein of the Otx subfamily, and in particular of an Otx2 homeoprotein, or of a composition comprising said homeoprotein, at a dose that is effective for improving the survival of said ganglionic neurons.

The present invention may in particular be used in patients who do not exhibit any photoreceptor neuron degeneration.

The subject of the present invention is also the use of a homeoprotein of the bicoid family, preferably of a homeoprotein of the Otx subfamily, and in particular of an Otx2 homeoprotein, or of a composition comprising said homeoprotein, for increasing the survival of retinal ganglion neurons in culture.

To implement the present invention, it is sufficient to bring said homeoprotein into contact with the ganglionic neurons; it in fact penetrates into said neurons by virtue of the internalization sequence present in its third helix. Preferably, said contact is brought about at a concentration of said homeoprotein of from 0.5 to 10 nM, advantageously from 1 to 5 nM, and particularly advantageously from 1.5 to 3 nM.

In vitro, it is sufficient to add said homeoprotein to the culture medium of the neurons. In vivo, it can be administered by various routes, locally, in particular by injection or infusion into the vitreous humor, or into the infraorbital space, or in the form of an eyewash or of an ophthalmic ointment. It can also be administered using a controlled-release device, for example in the form of an intraocular implant. Where appropriate, it can be administered systemically, for example by intravenous injection.

The doses of homeoprotein to be administered in vivo in order to obtain the desired concentration in contact with the ganglionic neurons can be readily determined and adjusted by those skilled in the art depending, in particular, on the methods of administration envisioned.

This contact can also be brought about by placing the ganglionic neurons in the presence of cells transformed so as to express or overexpress, and secrete, said homeoprotein. In vitro, this can be carried out by coculturing these transformed cells with ganglionic neurons. In vivo, cells transformed so as to express or overexpress, and secrete, said homeoprotein can, for example, be grafted into the retina.

It is also possible, where appropriate, to combine said homeoprotein with one or more other therapeutic active ingredients, in a joint or separate administration. For example, in the context of glaucoma treatment, it can be combined with a molecule or a combination of molecules used in this treatment, such as, for example, those described by Woodward & Chen (2007, mentioned above), and in particular a molecule or a combination of molecules capable of reducing intraocular pressure. The present invention encompasses, in particular, compositions which combine said homeoprotein with said active ingredient(s).

The present invention will be understood more clearly from the further description which follows, which refers to examples demonstrating the activity of an Otx2 homeoprotein on ganglionic neuron survival.

EXAMPLE 1: PRODUCTION AND PURIFICATION OF RECOMBINANT OTX2

The sequence encoding isoform-1 (SwissProt P32243) of the human Otx2 homeoprotein was cloned, under the control of the isopropyl-β-D-thiogalactoside (IPTG)-inducible trc promoter, into the plasmid pTchTEV2 (derived from a plasmid pTrcHis2 (Invitrogen), by replacement of the NcoI-HindIII segment with a linker which allows the insertion of a PCR product containing the Otx2 coding sequence upstream of and in frame with the cleavage site for the rTEV protease, followed by the myc-his6 tag in the C-terminal position, so as to produce the plasmid pTrOtx2hTev). The recombinant protein expressed by pTrOtx2hTev contains the Otx2 sequence fused in the C-terminal position to a Myc tag and a 6×His tag. It was produced in the *E. coli* strain BL21 CodonPlus-RP (Novagen) plus RP" transformed by heat shock. After selection of the transformed bacteria on agar-LB-ampicillin Petri dishes at 37° C. overnight, the expression of the recombinant protein is induced by overnight incubation at 37° C. in the autoinduction culture medium (IPTG-like) OverNight Express Instant TB Medium (Novagen). After centrifugation, the bacteria are taken up, on ice, in a lysis buffer (buffer: 20 mM NaPO$_4$, 0.5 mM NaCl, with protease inhibitors and without EDTA), at 3 ml of buffer per gram of bacterial pellet and lysed by being passed through a French press at 1000 psi, three times. The bacterial lysate is centrifuged and the supernatant is recovered and filtered through 0.45 µm. The proteins are purified on a 1 ml Hitrap Chelating HP column (Amersham) loaded with 0.1 M NiSO$_4$, and the supernatant is passed through at 0.5 ml/min. Two washes are carried out with the buffer containing imidazole at 10 mM, then at 50 mM. The elution is carried out by means of 10 fractions of 1 ml of buffer with imidazole at 250 mM. A final elution is carried out with the buffer and imidazole at 1 M. The purity of the elution fragments was verified by SDS-PAGE electrophoresis, then staining with Coomassie blue.

Their specificity was analyzed by Western blotting: two µL of each elution fraction were mixed with Laemmli buffer and boiled for 5 minutes. The protein separation was carried out by SDS-PAGE electrophoresis on 12% acrylamide gels. The proteins are electroblotted onto nitrocellulose membrane. After saturation in a buffer containing 5% of milk and 0.1% of Tween-20 in 1×PBS, the membrane is incubated with the primary antibody (rat polyclonal anti-Otx2 at 1/200 or mouse monoclonal anti-Myc at 1/1000) overnight at 4° C. After rinsing, the filter is incubated with the secondary antibody coupled to peroxidase (HRP), for 1 h. The enzyme activity of the peroxidase is revealed by chemiluminescence.

The analysis by Western blotting with the anti-HPX, or anti-Myc primary antibody makes it possible to reveal a single strong band of migration at the expected molecular weight (approximately 40 kDa) for the HPX protein with the Myc and 6×His tags.

The 3 fractions richest in Otx2 are combined: the Otx2 concentration thereof is approximately 200 µg/ml. The preparation thus obtained is dialyzed against a Tris 50 mM/EDTA 0.5 mM/NaCl 200 mM buffer and stored at −20° C. in this same buffer containing 45% glycerol. The glycerol is removed before each experiment by dialysis against the culture medium.

EXAMPLE 2: EFFECT OF OTX2 ON THE SURVIVAL OF AXOTOMIZED RETINAL GANGLION NEURONS

Retinal Cell Cultures

The effect of the protein was tested on retinal neurons after dissociation and culture. Two protocols were used: firstly, mixed cultures comprising all the retinal cell types; secondly, purified ganglionic neuron cultures.

All the mixed culture experiments were carried out on adult C57B16 mice (from 6 to 10 weeks old), and all the purified retinal ganglion cell culture experiments were carried out on 8-week-old adult Long-Evans rats. The mice and the rats were sacrificed by euthanasia by cervical dislocation. The eyes were removed within less than 15 minutes, after periorbital disinfection with Mucocit (Bioblock), by intraorbital dissection of the eyeball. The procedures used are in accordance with the recommendations of the EEC (86/609/EEC) and the French National Committee for the use of laboratory animals.

Mixed Cultures of Dissociated Adult Retinal Cells

The protocol used is that described by Gaudin et al. (Invest Ophthalmol V is Sci, 37, 2258-2268, 1996).

Sterile glass coverslips are pretreated with Poly-D-Lysine (Sigma P-6407) at 2 µg/cm$^2$ overnight at 37° C. and then laminin (Sigma L-2020) at 1 µg/cm$^2$, for 3 hours at 37° C.

The retinas are dissected in CO$_2$-independent medium without L-glutamine (Gibco 18045-054). The retinas are cut into pieces with scissors, rinsed with PBS without Ca2+, Mg2+ (Invitrogen 14190-185) with 0.6% glucose and 0.5 mM EDTA, and incubated in the presence of 0.2% papain (Worthington Biochemicals, 1 unit for a tube containing 10 retinas), for 15 minutes at 37° C. The papain was activated (30 minutes at 37° C.) by adding 1 unit of papain to 24 µL of papain-activating solution containing 1.1 mM of EDTA, 0.067 mM of β-mercaptoethanol and 5.5 mM of L-cysteine. The hydrolysis is stopped by adding 1 ml of stop medium (Neurobasal A medium [Invitrogen 10888-022] and 10% fetal calf serum (FCS) [Invitrogen 10270-098]), after having added DNase I (Sigma, 5 µg/ml). The cells are dissociated, with a ground Pasteur pipette, in the stop medium, counted with Trypan blue to exclude the dead cells, seeded at various cell densities (from 75 000 to 400 000 cells per well) and maintained in culture for 6 days. The recombinant Otx2 protein is dialyzed, prediluted in the culture medium and distributed into the wells at various concentrations just before the cell seeding. The serum-free culture medium is composed of Neurobasal A medium (NBA) (Gibco 10888) supplemented with: 5 µM L-glutamine (Sigma G-6392), 2.5 µM B27 complement (Gibco 17504-044), 2.5 µM glutamate-aspartate (Gibco), antibiotic/antimycotic (Gibco 15240-096). The culturing is carried out at 37° C. in incubators at 95% air and 5% CO$_2$. On the 6$^{th}$ day of culturing, the cells are fixed in 4% paraformaldehyde (PAF) for 15 minutes and then rinsed 3 times with PBS and stored at 4° C. until the immunocytochemistry is carried out.

The RGCs surviving after 6 days in mixed culture are identified by virtue of their immunoreactivity with respect to two complementary markers: anti-neurofilament 200 antibody (NF-200; Sigma N-0142) and anti-neurofilament 68 antibody (NF-68; Sigma N-5 139). They have a respective specificity of 91% and 88% (Kong and Cho, Life Sci, 64, 1773-1778, 1999). Their respective sensitivity on large RGCs (size >21 µm) is 94% and 100%. They have a sensitivity of 64% and 84% on small RGCs (size <14 µm) (Ruiz-Ederra et al., Mol V is, 10, 83-92, 2004). Morphological criteria are also used: RGCs have a variable size, and a round shape with an off-center nucleus.

The procedures are carried out at ambient temperature. The cells (fixed on D6) are permeabilized for 5 minutes in PBS with 0.2% Triton X-100, rinsed in PBS 3 times, saturated for 30 minutes in PBS with 10% FCS (PBS-FCS buffer), and then incubated with the primary antibody or antibodies, diluted in the same buffer, for 2 hours. The cells are then rinsed 3 times in PBS and incubated for 1 hour with the secondary antibody or antibodies.

The results obtained are illustrated by FIG. 1. Maximum survival (×3) is observed at 50 ng/ml, i.e. 1.65 nM. An effect is visible from 0.7 nM onward.

Cultures of Adult Retinal Ganglion Cells Purified by Immunopanning on the Thy-1 Antibody The protocol used is that described by Barres et al., (Neuron, 1, 791-803, 1988).

The pretreatment of the coverslips and the serum-free culture medium are the same as for the mixed cultures. Unless specified, the various incubations are carried out at ambient temperature.

Preparation of the Cell Suspension

The retinas are dissected in D-PBS (Invitrogen 14287-080). The retinas are rinsed with D-PBS, and then incubated in the presence of papain (Worthington Biochemicals, 165 units for a tube containing 12 retinas), for 30 minutes at 37° C. The papain was activated for 5 minutes at 37° C. by adding 165 units of papain to 5 ml of D-PBS and 1000 units of DNase (Sigma D4527). The hydrolysis is stopped by adding 4 ml of 0.15% ovomucoid. The cells are dissociated with a ground Pasteur pipette, in a 0.15% ovomucoid solution, in the presence of DNase and of rabbit anti-rat macrophage primary antibody (France Biochem AIA5 1240). The cell suspension thus dissociated and preincubated is centrifuged, taken up in 15 ml of D-PBS with 0.02% BSA (Sigma A8806), and then filtered through a 48tm Nitex filter (Dutscher 074011).

Preparation of Panning Dishes and Antibodies Used

During the overnight period preceding the dissection of the retinas, two Petri dishes termed "A" (150 mm, Dutscher 35-1058) are incubated with 20 ml of 50 mM Tris-HCl solution, pH 9.5, and 60 µL of the goat anti-rabbit IgG secondary antibody (Interchim 111-005-003), and one Petri dish termed "B" (100 mm, Dutscher 35-1029) is incubated with 10 ml of 50 mM Tris-HCl solution, pH 9.5, and 30 µL of the goat anti-mouse IgM secondary antibody (Interchim 1 15-005-020). Each panning dish is then washed 3 times with PBS. The A dishes are then saturated with D-PBS/0.2% BSA. The B dish is incubated for 3 hours with the mouse anti-Thy1 IgM (T1 1D7, ECACC hybridoma), and then washed 4 times with D-PBS.

$1^{st}$ Panning Step: Subtraction of Macrophages

The cell suspension, preincubated with the rabbit anti-rat macrophage IgG primary antibody, is incubated with the goat anti-rabbit IgG secondary antibody on the first A dish for 36 minutes. The nonadherent cells are transferred onto the second A dish for a second incubation for 33 minutes.

$2^{nd}$ Panning Step: Selection of RGCs

The nonadherent cells are filtered through a 48 µm Nitex filter and incubated for 45 minutes on the B dish containing the mouse anti-Thy1 IgM primary antibody. The B dish is then washed several times (at least 10 times) with D-PBS so as to progressively dislodge the nonadherent cells. This progression is monitored under a microscope.

Step of Detaching the Purified Adherent Cells with Trypsin

The B dish is rinsed twice with Earle's Balanced Salt Solution (EBSS) (Sigma E6267) preheated to 37° C. The adherent cells on the B dish are incubated with a trypsin solution containing 4 ml of EBSS and 200 µL of 2.5% trypsin (Sigma T9201), for 10 minutes at 37° C. The trypsin is inactivated with a solution of 4 ml of D-PBS-30% fetal bovine serum (FBS). The cells are detached by gently pipetting with the trypsin-blocking solution, and then centrifuged and counted (exclusion of the dead cells with Trypan blue).

Otx2 is dialyzed, prediluted in the culture medium and then deposited into the wells before seeding of the cells at a density of 20 000 per well. In some experiments, Otx2 was preincubated with an anti-Otx2 polyclonal antibody (Neuromics) at 1/1000, for 30 minutes at 37° C.

A cell survival test is carried out on D1 in order to evaluate the average number of live RGCs initially seeded per well (on 4 coverslips), and then on D6 in order to evaluate the proportion of cells having survived in culture under the various conditions (3 to 6 coverslips per condition). The purified RGCs are incubated for 2 hours at 37° C. with a mixture of two reagents: calcein AM and ethidium (Live Dead Viability Cytotoxicity Kit, Invitrogen, L3224). The calcein AM fluoresces (green) only if it penetrates into a live cell where it is hydrolyzed to fluorescent calcein. The ethidium penetrates only into dead cells with damaged membranes and fluoresces red only by interacting with their DNA. The two markers fluoresce only if they penetrate into cells; there is consequently no background noise. The analysis is carried out directly under a microscope by transposing the coverslips (8 mm) onto coverslip carriers that are specially for this purpose, in 75 µl, of the culture medium incubated at 37° C. with the reagents of the live-dead test.

Figure 2:
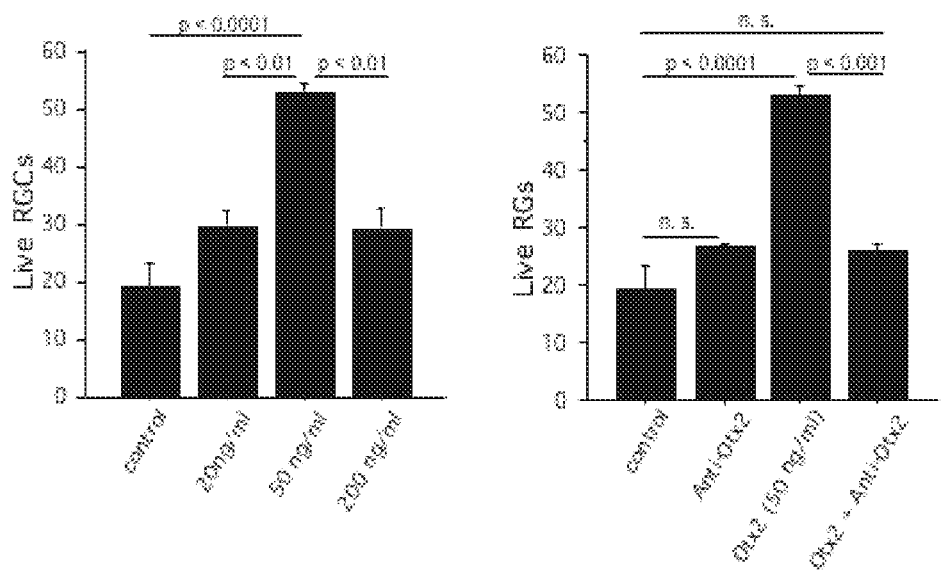
FIG. 2 is the results obtained from Cultures of adult retinal ganglion cells purified by immunopanning on the Thy-1 antibody.

FIG. 2 illustrates the results obtained. These results show that the same concentration of 1.65 nM is optimal for survival (×3) and that the effect of Otx2 is canceled out after preincubation of the protein with the anti-Otx2 neutralizing antibody, which has no effect by itself. The survival effect is therefore indeed due to Otx2 and not to a possible contaminant.

EXAMPLE 3: COMPARISON OF THE EFFECTS OF OTX2, OF MIXED RETINAL CULTURE-CONDITIONED MEDIUM, AND OF BDNF ON THE SURVIVAL OF RETINAL GANGLION NEURONS

The effects of Otx2 on the survival of ganglionic neurons were compared with those of adult ganglionic neuron survival factors previously described in the literature: mixed retinal culture-conditioned medium (Fuchs et al., Invest Ophthalmol V is Sci, 46, 2983-2991, 2005), and BDNF (Brain Derived Neurotrophic Factor) (Johnson et al., J Neurosci, 6, 3031-3038, 1986).

The experiments were carried out on cultures of adult ganglion cells purified by immunopanning, as described in example 2 above.

Otx2 and BDNF were used at the concentration of 50 ng/ml in the culture medium.

The mixed retinal culture-conditioned medium is prepared from mixed cultures prepared according to the protocol described in example 2 above. The initial culture medium contains 10% of FCS so as to allow the proliferation of the Müller glial cells. The cells are cultured under these conditions until confluence (approximately 10 days). After 4 washes with NBA, the culture medium is changed for a serum-free, chemically defined culture medium (NBA+2% B27) for a further 2 days. This conditioned medium (CM) is then recovered, centrifuged, aliquoted and then frozen in liquid nitrogen.

Figure 3:
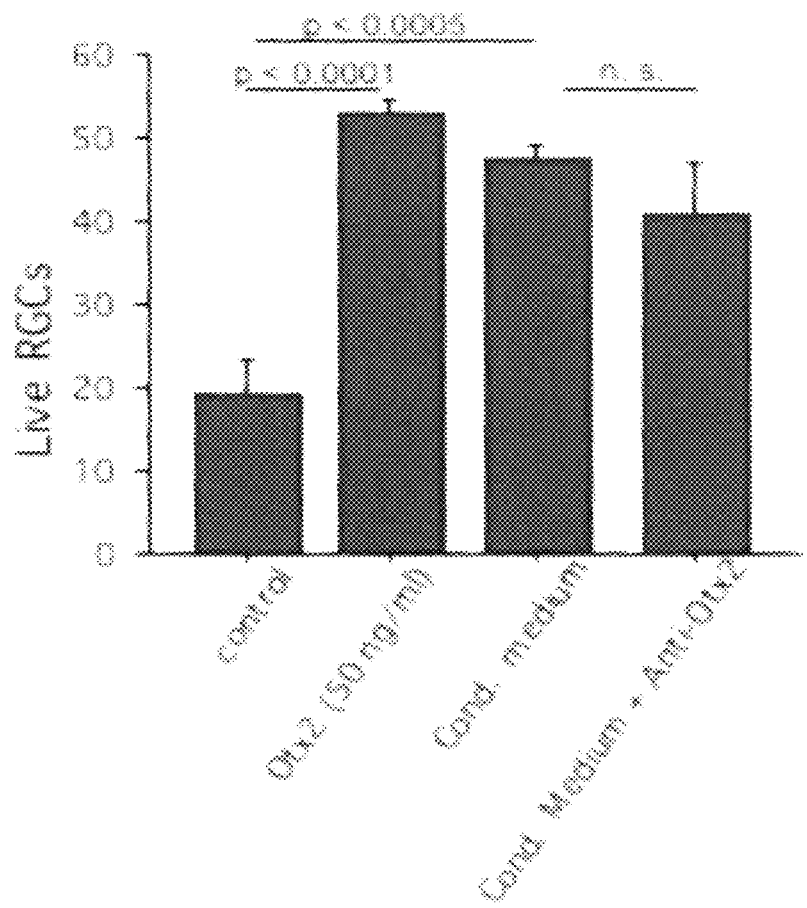
FIG. 3 is the results obtained from comparison of the effects of Otx2, of mixed retinal culture-conditioned medium, and of BDNF on the survival of retinal ganglion neurons.

The results are illustrated by FIG. 3. These results show that Otx2 at 50 ng/ml (1.65 nM) is as effective, if not more effective, than the conditioned medium. Preincubation of the conditioned medium with the anti-Otx2 antibody does not modify its effect, which demonstrates that this effect is not due to its Otx2 content. BDNF (Brain Derived Neurotrophic Factor) at 50 ng/ml gives an activity similar to that of the conditioned medium (results not shown).

It emerges from the experiments described above that Otx2 is a new survival factor for adult ganglionic neurons, and that its activity is equal to or greater than that of BDNF or of the conditioned medium.

EXAMPLE 4: EFFECTS OF OTX2 ON THE IN VIVO SURVIVAL OF RETINAL GANGLION NEURONS

The effect of Otx2 on the survival of retinal ganglion neurons was determined in vivo in a murine model.

The model chosen is N-methyl-D-aspartate (NMDA) poisoning. The ganglionic neuron survival was determined by measuring the level of expression of Brain 3A (Brn3A), a transcription factor which, in the retina, is specifically expressed in the ganglionic neurons, RGCs (Xiang et al., J. Neurosci., 15, 4762-4785, 1995).

C57B16 mice received, in the right eye, 1 µl of injection buffer (PBS or 9% NaCl) containing either 30 ng of Otx2, or 1 mM of NMDA, or 1 mM of NMDA supplemented with 3 ng or with 30 ng of Otx2, and, in the left eye, the same volume of injection buffer, without additive.

After 4 days, the animals are sacrificed, the retinas are removed, and the mRNA is extracted therefrom.

The level of expression of the Brn3A mRNA was determined by quantitative RT-PCR using the hypoxanthine phosphoribosyltransferase (HPRT) gene as reference gene, and the ratio between the expression of the Brn3A mRNA in the right eye and in the left eye was calculated.

Figure 4:
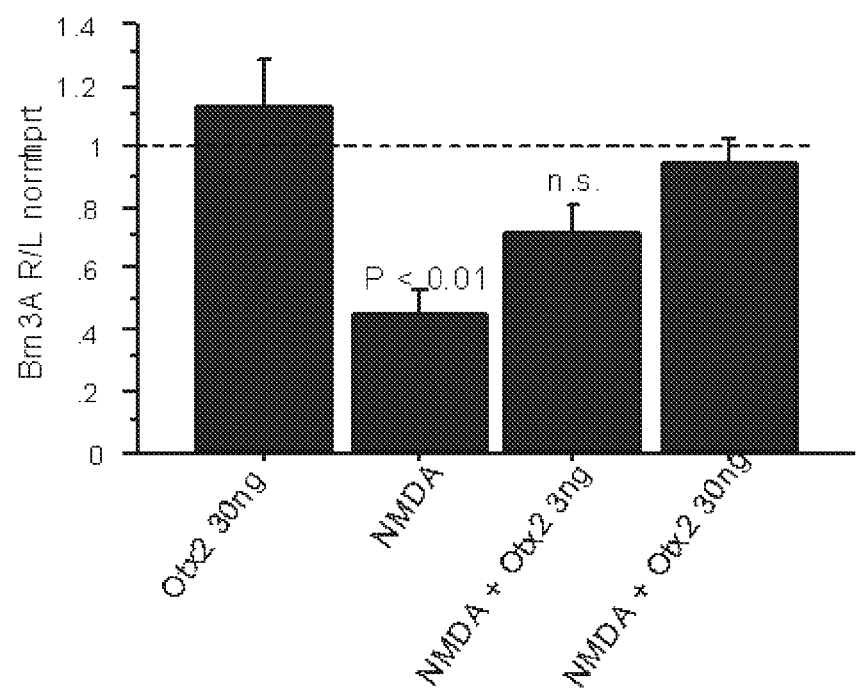
FIG. 4 is the results obtained from the effects of Otx2 on the in vivo survival of retinal ganglion neurons.

The results are illustrated by FIG. 4. The additives used are indicated along the X axis; the ratio between the amounts of Brn3A mRNA (normalized relative to the HPRT mRNA) in the right eye and in the left eye is indicated along the Y axis.

These results show that Otx2 alone has no significant effect on the level of expression of Brn3A (and therefore on the amount of ganglionic neurons) in the retina. NMDA, administered alone, significantly decreases (by approximately 60%) the amount of ganglionic neurons, and the addition of 3 ng of Otx2 does not significantly decrease the toxic effects of NMDA. On the other hand, the addition of 30 ng of Otx2 completely protects the ganglionic neurons against the toxic effects of NMDA.

The invention claimed is:

1. A method of reducing excitotoxicity-induced retinal ganglion neuron degeneration in a subject in need thereof, comprising administering into an eye of said subject a functional orthodenticle homolog 2 (Otx2) homeoprotein having a polypeptide sequence at least 90% identical to the amino acid sequence of SEQ ID NO: 1 or SEQ ID NO: 2 in a total amount of 30 ng by injection or infusion into the vitreous humor, into the infraorbital space, or in the form of an eyewash or an ophthalmic ointment, wherein the subject does not exhibit photoreceptor neuron degeneration, and the functional Otx2 homeoprotein has a homeodomain having at least 98% sequence identity with residues 38-97 of the amino acid sequence of SEQ ID NO: 1.

2. The method according to claim 1, wherein said excitotoxicity-induced retinal ganglion neuron degeneration occurs in glaucoma.

3. The method according to claim 1, wherein said functional Otx2 homeoprotein has a polypeptide sequence having the amino acid sequence of SEQ ID NO: 1 or SEQ ID NO: 2.

4. The method according to claim 1, wherein the subject suffers from glaucoma.

5. A method of reducing excitotoxicity-induced retinal ganglion neuron degeneration in a patient in need thereof, said method comprising
   selecting a patient who does not exhibit photoreceptor neuron degeneration, and
   administering into an eye of said patient a functional orthodenticle homolog 2 (otx2) homeoprotein having a polypeptide sequence at least 90% identical to the amino acid sequence of SEQ ID NO: 1 or SEQ ID NO: 2 in a total amount of 30 ng by injection or infusion into the vitreous humor, into the infraorbital space, or in the form of an eyewash or an ophthalmic ointment,
   wherein the functional Otx2 homeoprotein has a homeodomain having at least 98% sequence identity with residues 38-97 of the amino acid sequence of SEQ ID NO: 1.

6. The method according to claim 5, wherein said excitotoxicity-induced retinal ganglion neuron degeneration occurs in glaucoma.

7. A method of increasing survival of retinal ganglion neurons in culture comprising contacting isolated retinal ganglion neurons with a functional orthodenticle homolog 2 (Otx2) homeoprotein having a polypeptide sequence at least 90% identical to the amino acid sequence of SEQ ID NO: 1 or SEQ ID NO: 2 at a concentration of 0.5 to 10 nM, wherein the functional Otx2 homeoprotein has a homeodomain having at least 98% sequence identity with residues 38-97 of the amino acid sequence of SEQ ID NO: 1.

8. The method according to claim 7, wherein said functional Otx2 homeoprotein has a polypeptide sequence having the amino acid sequence of SEQ ID NO: 1 or SEC) ID NO: 2.

* * * * *